United States Patent [19]

Mason et al.

[11] Patent Number: 5,580,766
[45] Date of Patent: Dec. 3, 1996

[54] RETROVIRAL VECTOR PARTICLES FOR TRANSDUCING NON-PROLIFERATING CELLS

[75] Inventors: James M. Mason, Wallingford; Scott P. Kennedy, Southington, both of Conn.; Seth A. Fidel, Mount Kisco, N.Y.

[73] Assignee: Alexion Pharmaceuticals, Inc., New Haven, Conn.

[21] Appl. No.: 181,335

[22] Filed: Jan. 14, 1994

[51] Int. Cl.$^6$ .............................. C12N 15/86; C12N 5/10; C12P 21/00; C07H 21/04

[52] U.S. Cl. ................................ 435/172.1; 435/240.2; 435/320.1; 435/69.1; 435/172.3; 435/235.1; 536/23.1; 536/23.4; 536/23.72; 536/24.1

[58] Field of Search ............................. 435/69.1, 172.1, 435/172.3, 240.2, 320.1, 235.1; 536/23.1, 23.4, 23.72, 24.1

[56] References Cited

PUBLICATIONS

Bonnerot, et al., "A β-galactosidase hybrid protein targeted to nuclei as a marker for developmental studies" *Proc. Natl. Acad. Sci. USA*, 84:6795–6799, 1987.

Bowerman et al., "A nucleoprotein complex mediates the integration of retroviral DNA" *Genes & Development*, 3:469–478, 1989.

Bukrinsky, et al., "Active nuclear import of human immunodeficiency virus type 1 preintegration complexes" *Proc. Natl. Acad. Sci. USA*, 89:6580–6584, 1992.

Bukrinsky, et al., "Associate of integrase, matrix and reverse transcriptase antigensof human immunodeficiency virus type 1 with viral nucleic acids following acute infection" *Proc. Natl. Acad. Sci. USA*, 90:6125–6129, 1993.

Bukrinsky, et al., "A nuclear localization signal within HIV–1 matrix protein that governs infection of non–dividing cells" *Nature*, 365:666–669, 1993.

Dingwall and Laskey, "Protein Import into the Cell Nucleus" *Ann. Rev. Cell Biol.*, 2:367–390, 1986.

Dingwall, et al., "The Nucleoplasmin Nuclear Location Sequence is Larger and More Complex than That of SV–40 Large T Antigen" *J. Cell Biol.*, 107:841–849, 1988.

Forbes, "Structure and Function of the Nuclear Pore Complex" *Annu. Rev. Cell Biol.*, 8:495–527, 1992.

Galileo, et al., "Neurons and glia arise from a common progenitor in chicken optic tectum: Demonstration with two retroviruses and cell type–specific antibodies" *Proc. Natl. Acad. Sci. USA*, 87:458–462, 1990.

Kalderon, et al., "A Short Amino Acid Sequence Able to Specify Nuclear Location" *Cell*, 39:499–509, 1984.

Lewis and Emerman, "Passage through Mitosis is Required for Oncoretroviruses but Not for the Human Immunodeficiency Virus" *J. Virol.*, 68:510–516, 1993.

Roe et al., "Integration of murine leukemia virus DNA depends on mitosis" *EMBO J.*, 12:2099–2108, 1993.

Springett et al., "Infection Efficiency of T Lymphocytes with Amphotropic Retroviral Vectors is Cell Cycle Dependent" *J. Virol.*, 63:3865–3869, 1989.

Varmus and Brown, *Retroviruses*, pp. 53–108 in Berg and Howe, (eds), 1989, Mobile DNA, American Society for Microbiology, Washington, DC.

*Primary Examiner*—David Guzo
*Attorney, Agent, or Firm*—Seth A. Fidel; Maurice M. Klee

[57] ABSTRACT

Retroviral vector particles are provided which contain: 1) oncoretroviral gag, pol, and env proteins, including an oncoretroviral gag capsid protein which has been mutated so as to contain a nuclear localization signal (NLS) sequence; and 2) at least one exogenous gene. The particles can be used to transduce non-proliferating cells, including stem cells and neurons. The presence of the NLS sequence allows the at least one exogenous gene to enter into the nucleus of a target cell, thus allowing integration of the gene into the genome of the target cell.

7 Claims, 3 Drawing Sheets

RETROVIRAL VECTOR PARTICLES FOR TRANSDUCING NON-PROLIFERATING CELLS

FIELD OF THE INVENTION

The present invention relates to the transduction of cells using retroviral vector particles and, in particular, to the transduction of non-proliferating cells using such particles.

BACKGROUND OF THE INVENTION

I. Retroviruses

The Retroviridae virus family encompasses all viruses containing an RNA genome and producing an RNA-dependent DNA polymerase (reverse transcriptase). The family is divided into three subfamilies: (1) Oncovirinae, including all the oncogenic retroviruses (referred to in the older literature as "oncornaviruses") and several closely related nononcogenic viruses (collectively referred to herein as "oncoretroviruses"); (2) Lentivirinae, the "slow retroviruses," such as the human immunodeficiency virus (HIV) and visna virus; and (3) Spumavirinae, the "foamy" retroviruses that induce persistent infections, generally without causing any clinical disease. More detailed descriptions of the retroviruses may be found in Weiss et al., (eds), *RNA Tumor Viruses*, Cold Spring Harbor Laboratory, N.Y., 1985; Doolittle, et al., *Quart. Rev. Biol.*, 64:1–29, 1979; and Varmus and Brown, *Retroviruses*, p. 53–108, in Berg and Howe, (eds), 1989, *Mobile DNA*, American Society for Microbiology, Washington, D.C.

In broadest overview, the life cycle of a retrovirus comprises entry of an infectious retroviral particle into a host cell, integration of the virus' genetic information into the host cell's genome, and production of new infectious retroviral particles by the biosynthetic machinery of the infected host cell. More specifically, upon entering a cell, a retroviral particle initiates a series of interactive biochemical steps that results in the production of a DNA copy of the virus' RNA genome and its integration into the nuclear DNA of the cell. This integrated DNA copy is referred to as a provirus and can be inherited by any daughter cells of the infected cell like any other gene. See Goff, *Annu. Rev. Genet.*, 26:527–544, 1992.

All retroviral particles share common morphological, biochemical, and physical properties, including:

(1) A linear, positive-sense, single-stranded RNA genome composed of two identical subunits and making up about 1% of the mass of the virus.

(2) At least three types of proteins encoded by the viral genome, i.e., gag proteins (the group antigen internal structural proteins), pol proteins (the RNA-dependent DNA polymerase and the protease and integrase proteins), and env proteins (the viral envelope protein or proteins). These proteins together make up about 60%–70% of the mass of the virus.

(3) Lipid derived from the cell membrane of an infected cell making up about 30%–40% of the mass of the virus.

(4) Carbohydrate associated with the env proteins, making up about 2–4% of the mass of the virus.

(5) An overall spherical morphology with variable surface projections.

(6) An isocahedral capsid structure containing a ribonucleoprotein complex within an internal nucleoid or nucleocapsid shell.

In addition to genes encoding the gag, pol, and env proteins, the genome of the retrovirus includes two long terminal repeat (LTR) sequences, one at each end of the linear genome. These 5' and 3' LTRs serve to promote transcription and polyadenylation of viral mRNAs and participate in the integration of the viral genome into the genomic DNA of the infected host cell. Adjacent to the 5' LTR are sequences necessary for reverse transcription of the viral genome (the tRNA primer binding site) and the $\psi$ site, a sequence that directs the encapsulation of viral RNA into retroviral particles (virions). See Mulligan, In: *Experimental Manipulation of Gene Expression*, Inouye (ed), 155–173, 1983; Mann, et al., *Cell*, 33:153–159, 1983; Cone, and Mulligan, Proceedings of the National Academy of Sciences, U.S.A., 81:6349–6353, 1984.

The protein products encoded by the gag, pol, and env genes are generally synthesized by the infected cell as polyproteins that are subsequently cleaved to produce the final separate protein products. In particular, the translation products of the oncoretroviral gag genes are generally produced as a 60–80 kDa polyprotein translation product that is subsequently cleaved to form at least three gag proteins, including the matrix (MA), capsid (CA) and nucleocapsid (NC) proteins.

The gag proteins of specific oncoretroviruses are often referred to in the art by the prefix p followed by a number representing their approximate molecular weight in kilodaltons. For example, the four gag proteins of the Moloney murine leukemia virus (MoMLV) are referred to as p10 (NC), p12, p15 (MA), and p30 (CA).

The gag matrix and capsid proteins have multiple functions. Late in infection, after integration of the viral genetic material into the host cell genome, they both play essential roles by contributing to the structure of nascent viral particles. Earlier in infection, they participate in the transfer of the DNA copy of the virus' genome into the host cell's genome. They carry out this function as part of nucleoprotein structures referred to in the art as "nucleoprotein complexes" or "preintegration complexes." These complexes assemble in the host cell's cytoplasm and comprise the DNA copy of the virus' genome, the viral integrase protein, and either or both of the MA and CA proteins. See Bowerman et al., *Genes & Development*, 3:469–478, 1989; Bukrinsky, et al., *Proc. Natl. Acad. Sci. USA*, 89:6580–6584, 1992; and Bukrinsky, et al., *Proc. Natl. Acad. Sci. USA*, 90:6125–6129, 1993.

II. The Preintegration Complex

Integration of the DNA of the preintegration complex into the host cell's genome generally requires that the complex come into close proximity with the host's genomic DNA. The genomic DNA of the host cell, however, is generally sequestered in the cell's nucleus, within the bounds of the nuclear envelope.

For oncoretroviruses, the breakdown of the nuclear envelope during the process of mitotic cell division is believed to allow access of the preintegration complex to the host's genomic DNA, as reported, for example, in Roe, T., et al., *EMBO J.*, 12:2099–2108; 1993; and in Lewis and Emerman, J., *Virol.*, 68:510–516, 1993. Accordingly, these retroviruses only replicate efficiently in cells which proliferate.

In the lentiretroviruses, specifically, HIV, the preintegration complex is able to enter the nucleus of non-proliferating host cells, such as neurons (see, for example, Lewis and Emerman, 1993, supra. It has been reported by Bukrinsky, et al., 1992, supra, that the entry of the HIV preintegration complex into the nucleus involves a rapid, ATP-dependent process that is independent of cell division. It is believed that this active entry of the HIV preintegration complex is mediated by a nuclear localization signal (NLS) sequence (see below) that is found near the amino terminus of the gag MA protein, which, for HIV, is associated with the preintegration complex. See Bukrinsky, et al., 1993, supra; and Bukrinsky, et al., *Nature*, 365:666–669, 1993.

With regard to the present invention, it is notable that the structure of the HIV preintegration complex differs from that of the MoMLV preintegration complex, and that the gag capsid protein, which has been reported to be absent from the HIV preintegration complex, is found in the MoMLV preintegration complex (Bukrinsky, et al., *Proc. Natl. Acad. Sci. USA*, 1993, Supra; and Bowerman, et al., 989, supra).

III. Nuclear Localization Signal Sequences

Various proteins whose functions require entry into the cell nucleus are known to include nuclear localization signal (NLS) sequences. These sequences are, in general, short in length and positively charged (basic), and thus have been referred to in the art as having basic domains. They serve to direct the entire protein in which they occur to the cell's nucleus.

Amino acid sequences have been determined for the nuclear localization signals of a variety of proteins found in the cells of vertebrates. For example, the NLS within the amino acid sequence of the SV40 (monkey virus) large T antigen was reported by Kalderon, et al., *Cell*, 39:499–509, 1984 (see SEQ.1). This "single basic domain" SV40 NLS is considered the canonical prototype signal to which all others have been compared (Kalderon, 1984, supra; Forbes, *Annu. Rev. Cell Biota.*, 8:495–527, 1992), and many NLSs resemble it. Many other NLSs, however, more closely resemble the first identified NLS, that of the *Xenopus* (African clawed toad) protein, nucleoplasmin. This "double basic domain" NLS (see SEQ. 2) was initially defined by protease digestion of nucleoplasmin by Dingwall, et al., *Cell*, 30:449–458, 1982 (also see Dingwall, et al., *J. Cell Biol.*, 107:841–849; 1988).

Experiments have been performed in a number of laboratories in which the effects of NLSs incorporated in synthetic peptides or grafted onto reporter proteins not normally targeted to the cell nucleus have been studied. Localization studies revealed that the NLSs cause these peptides and reporter proteins to be concentrated in the nucleus. See, for example, Dingwall, and Laskey, *Ann. Rev. Cell Biol.*, 2:367–390, 1986; Bonnerot, et al., *Proc. Natl. Acad. Sci. USA*, 84:6795–6799, 1987; Galileo, et al., *Proc. Natl. Acad. Sci. USA*, 87:458–462, 1990; Forbes, 1992, supra.

IV. Gene Transfer by Oncoretroviral Transduction

Oncoretroviral vectors and packaging cells (helper cells) have been developed to efficiently introduce recombinant nucleic acid molecules into mammalian cells without the danger of the production of replicating infectious virus, i.e., to transduce target cells. These retroviral systems efficiently integrate DNA molecules containing some or all of the genetic information (sequence) of the introduced recombinant nucleic acid molecules (retroviral vector RNAs) into the genome of the target cell so that the introduced genetic material is replicated and is stably and functionally maintained in the cell. See Ausubel, et al., *Current Protocols in Molecular Biology*, Wiley Interscience, John Wiley and Sons, 1992.

Oncoretroviral vectors are particularly useful for genetically modifying mammalian cells, including primate cells, because of the high efficiency with which they can transduce target cells and integrate their genetic information into the target cell genome. Additionally, oncoretroviral vectors may be constructed so as to be capable of transducing mammalian cells from a wide variety of species and tissues. Medical applications of gene therapy mediated by retroviral vector particles are reviewed in Boggs, *Int. J. Cell Cloning*, 8:80–96, 1990; Kohn, et al., *Cancer Investigation*, 7:179–192, 1989; Lehn, *Bone Marrow Transplantation*, 5:287–293, 1990; Verma, *Scientific American*, pp. 68–84, 1990; Weatherall, *Nature*, 349:275–276, 1991; and Felgner and Rhodes, *Nature*, 349:351–352, 1991.

Successful gene transfer by transduction with an oncoretroviral vector particle requires: incorporation of the gene of interest into the vector; packaging of the vector into an oncoretroviral vector particle; binding of the oncoretroviral vector particle to the target cell; penetration into the cell; uncoating of the particle; reverse transcription of the viral RNA into DNA; integration of the DNA into the host genome (typically mediated by the viral integrase protein); and expression of the gene of interest.

Prior to the present invention, successful stable gene insertion into a target cell using oncoretroviral vectors has required that the target cell undergo at least one round of cell division (Springett et al., *J. Virol.*, 63:3865–3869, 1989; Roe et al., 1993, supra). Accordingly, to date, gene transfer by oncoretroviral transduction has been limited to proliferating cells. This limitation has represented a significant shortcoming of this technology.

SUMMARY OF THE INVENTION

In view of the foregoing state of the art, it is an object of the present invention to provide oncoretroviral vector particles which are able to transduce nonproliferating cells. It is a further object of the invention to provide packaging cells for producing such particles.

To achieve the foregoing and other objects, the invention provides retroviral vector particles comprising an oncoretroviral gag capsid protein which has been mutated so as to contain a nuclear localization signal. The invention also provides nucleic acid molecules encoding the mutated gag capsid proteins, as well as packaging cells for producing the retroviral vector particles of the invention. In addition, the invention provides methods for using the retroviral vector particles to introduce genes into target cells.

In certain preferred embodiments of the invention, the gag capsid protein is from the Moloney murine leukemia virus (MoMLV). The amino acid sequence for this protein is set forth in SEQ. ID NO:3.

In accordance with these embodiments, the NLS is preferably of the type found in SV40 as shown in SEQ.1 and SEQ. ID NO:4. Other NLSs which can be used in the practice of the invention include those disclosed in the Kalderon, 1984; Forbes, 1992; Dingwall, et al., 1988; and Dingwall and Laskey, 1986, references cited above. Other NLSs now known or subsequently identified may also be used in the practice of the invention.

Preferred mutated forms of the MoMLV gag capsid protein which include the SV40 NLSs of SEQ. ID NO:1 and SEQ. ID NO:4 are shown in SEQ. ID NO:5 and SEQ. ID NO:6, respectively.

BRIEF DESCRIPTION OF THE DRAWINGS

The accompanying drawings, which are incorporated in and constitute part of the specification, illustrate certain aspects of the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

As discussed above, the present invention relates to: packaging cells expressing a gag CA protein which has been mutated so as to contain an NLS; retroviral vector particles produced using such packaging cells; and gene transfer mediated by such retroviral vector particles.

General discussions of packaging cells, retroviral vector particles and gene transfer using such particles can be found in various publications including PCT Patent Publication No. WO 92/07943, EPO Patent Publication No. 178,220, U.S. Pat. No. 4,405,712, Gilboa, *Biotechniques*, 4:504–512, 1986; Mann, et al., *Cell*, 33:153–159, 1983; Cone and Mulligan, *Proc. Natl. Acad. Sci. USA*, 81:6349–6353 1984; Eglitis, et al., *Biotechniques*, 6:608–614, 1988; Miller, et al., *Biotechniques*, 7:981–990, 1989; Morgenstern and Land, *Nucleic Acids.Res.*, 18:3587–3596, 1990; Eglitis, *Human Gene Therapy*, 2:195–201; Miller, 1992, *Nature*, 357:455–460; Mulligan, 1993, *Science*, 260:926–932; and Ausubel, et al., 1992, Supra.

I. Packaging Cells/Retroviral Vector Particles

The packaging cells of the invention are produced by 1) constructing one or more expression vectors comprising recombinant nucleic acid molecules encoding the oncoretroviral pol and env proteins, as well as the gag proteins, including the mutated gag CA protein of the invention (hereinafter referred to as "packaging vectors"); 2) introducing the one or more packaging vectors into cultured cells, typically, mammalian cells; and 3) obtaining the desired packaging cells by selecting those cells of the culture which stably express proteins encoded by the one or more packaging vectors.

The manipulation of retroviral nucleic acids to construct packaging vectors and packaging cells is accomplished using techniques known in the art. See Ausubel, et al., supra, Volume 1, Section III (units 9.10.1–9.14.3), 1992; Sambrook, et al., *Molecular Cloning—A Laboratory Manual* (2nd Ed.), Cold Spring Harbor Laboratory, Cold Spring Harbor, 1989; Miller, et al., 1989, supra; Eglitis, et al., 1988, supra; U.S. Pat. Nos. 4,650,764, 4,861,719, 4,980,289, 5,122,767, and 5,124,263; and PCT Patent Publications Nos. WO 85/05629, WO 89/07150, WO 90/02797, WO 90/02806, WO 90/13641, WO 92/05266, WO 92/07943, WO 92/14829, and WO 93/14188.

These manipulations typically involve the use of DNA copies of the gag, pol, and env retroviral genes cloned in plasmid vectors. Such plasmid vectors containing retroviral genes can be prepared by, for example, isolation of DNA copies of the viral genome from the cytoplasm of infected cells (using, for example, the method of Hirt, *J. Mol. Biol.*, 26:365–369, 1967), restriction digestion of the DNA copies of the viral genome (or PCR amplification of regions of interest of the DNA, generally followed by restriction digestion of the PCR product) to produce desired fragments, and multiple rounds of subcloning of the fragments, along with fragments containing suitable selectable marker and origin of replication sequences, to produce operable plasmid vectors.

Multiple rounds of subcloning are used because it has been found that the typical bacterial cells used as plasmid hosts in subcloning, e.g., *E. coli*, tend to create deletions in the nucleotide sequences of newly inserted retroviral insert fragments when such fragments comprise more than about 4 kbp. Accordingly, construction of the final packaging vector proceeds more efficiently if small retroviral insert fragments (on the order of less than about 4 kbp) are sequentially assembled in the plasmid through multiple rounds of subcloning.

In accordance with the invention, a sequence encoding a mutated gag CA protein is included in one of the one or more packaging vectors used to construct the packaging cells. As discussed above, this mutated gag CA protein includes an NLS. The NLS can be one of those already known in the art, such as those referred to above, or can be one subsequently identified by, for example, monitoring the location within target cells of reporter proteins or peptides containing a candidate NLS sequence. See, for example, the Forbes, 1992; Dingwall, et al., 1988; Dingwall and Laskey, 1986; and Kalderon, et al., 1984, references cited above.

Preferably, short NLS sequences are used, e.g., sequences comprising less than about ten amino acids. The mutated gag CA protein can contain more, less, or the same number of amino acids as the non-mutated protein. The NLS sequence should be situated within the mutated molecule so that the biological function of the gag CA protein is not substantially impaired. Generally, locating the NLS sequence in the region of the carboxyl terminus of the gag CA protein is preferred. Also, substantially maintaining the length of the gag CA protein is preferred.

If desired, the gag CA protein can be mutated to include more than one NLS. However, in order to substantially maintain the normal function of the gag protein, the use of one NLS is generally preferred. Also, additional NLS sequences can be incorporated in other proteins found in the oncoretroviral preintegration complex, such as the pol integrase protein and the gag matrix protein if present in the preintegration complex. Such NLS sequences can be obtained by mutating the nucleic acid sequences encoding these proteins by means of the methods disclosed herein. Again, these mutations are made in a manner which substantially preserves the functional attributes of the protein which is mutated. In general, mutation of just the gag capsid protein is preferred.

Accordingly, as illustrated by the example set forth below, the NLS sequence is preferably obtained by:

(1) selecting a carboxyl terminal segment of the gag CA protein amino acid sequence which resembles an NLS sequence; and (2) mutating the nucleic acid sequence encoding that segment to generate amino acid substitutions in the segment which bring its sequence into closer conformance, preferably, identical correspondence, with the NLS sequence.

This procedure for designing the mutated protein, i.e., searching for regions which resemble an NLS sequence, may also be used to identify segments suitable for mutation located elsewhere within the protein besides the carboxyl terminus.

The mutation of the gag CA protein can be performed by various methods known in the art for creating defined alterations in nucleic acid sequences including, but not limited to, oligonucleotide directed mutagenesis, PCR mutagenesis (see example below), or synthetic gene construction. See Sambrook, et al., 1989, supra; Ausubel, et al., 1992, supra; Erlich, *PCR Technology,* Stockton Press, New York, 1989. These mutations can be created in the gag CA gene at any point in the process of constructing a packaging vector which codes for the gag CA protein, i.e., before, during, or after any of the subcloning steps used to join the various DNA fragments used in the construction of this packaging vector.

To form the packaging cells, the packaging vector or vectors are introduced into suitable host cells. Examples of such cells are found in, for example, Miller and Buttimore, *Mol. Cell Biol.,* 6:2895–2902, 1986; Markowitz, et al., *J. Virol.,* 62:1120–1124, 1988; Cosset, et al., *J. Virol.,* 64:1070–1078, 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. A preferred host cell is a cell from the NIH/3T3 mouse embryo fibroblast line, e.g. ATCC CRL 1658 cells.

Once a packaging cell line has been established, the next step is to generate "producer cells" by introducing retroviral vectors into the packaging cells. Examples of such retroviral vectors are found in, for example, Korman, et al., 1987, *Proc. Natl. Acad. Sci. USA,* 84:2150–2154; Miller and Rosman, *Biotechniques,* 7:980–990, 1989; Morgenstern and Land, 1992, supra; U.S. Pat. Nos. 4,405,712, 4,980,289, and 5,112,767; and PCT Patent Publications Nos. WO 85/05629, WO 90/02797, and WO 92/07943. The retroviral vector includes a ψ site and one or more exogenous nucleic acid sequences selected to perform a desired function, e.g., an experimental, diagnostic, or therapeutic function. These exogenous nucleic acid sequences are flanked by LTR sequences which function to direct high efficiency integration of the sequences into the genome of the ultimate target cell.

The producer cells generated by the foregoing procedures are used to produce the retroviral vector particles of the invention by culturing of the cells in a suitable growth medium. If desired, the particles can be harvested from the culture and administered to the target cells which are to be transduced, or the target cells can be co-cultured with the producer cells.

II. Gene Transfer

A. Genes

A variety of genes and DNA fragments can be incorporated into the retroviral vector particles of the invention for use in gene therapy. These DNA fragments and genes may encode RNA and/or protein molecules which render them useful as therapeutic agents. Proteins of use in gene therapy include various hormones, growth factors, enzymes, lymphokines, cytokines, receptors, and the like.

Among the genes which can be transferred in accordance with the invention are those encoding polypeptides that are absent, are produced in diminished quantities, or are produced in mutant form in individuals suffering from a genetic disease. Other genes of interest are those that encode proteins that have been engineered to circumvent a metabolic defect or proteins that, when expressed by a cell, can adapt the cell to grow under conditions where the unmodified cell would be unable to survive, or would become infected by a pathogen.

In addition to protein-encoding genes, the present invention can be used to introduce nucleic acid sequences encoding medically useful RNA molecules into cells. Examples of such RNA molecules include anti-sense molecules and catalytic molecules, such as ribozymes.

B. Target Cells

The retroviral vector particles of the invention can be used to introduce exogenous nucleic acid molecules into a variety of cells and tissues including, without limitation, endothelial cells, myeloid cells, bone marrow cells, stem cells (including hematopoietic and embryonic stem cells), lymphocytes, hepatocytes, fibroblasts, lung cells, muscle cells, embryonic cells, and nerve cells.

As stated above, the retroviral vector particles of the invention have the unique property of being able to efficiently transduce both proliferating and nonproliferating cells. This ability is a significant advantage of the invention because of the proliferation characteristics of many of the target cells which one would like to transduce with retroviral vectors. In particular, many important target cells may alter their properties in undesirable ways when they divide, or they may divide very slowly, or they may not divide at all.

For example, most neurons do not divide at all. Accordingly, prior oncoretroviral vector transduction systems could not efficiently be used with these cells. The retroviral vector particles of the invention, however, do not require cell proliferation and thus can be used to transduce neurons.

Endothelial cells which are contact inhibited, the usual state of such cells within the body, divide very slowly, if at all. Accordingly, the same considerations regarding transduction which apply to neurons also apply to endothelial cells.

Certain stem cells are known to divide slowly in culture, and all stem cells tend to differentiate into less useful cell types the longer they are kept in culture. Accordingly, it is desirable to transduce stem cells as quickly as possible without having to wait for them to divide in culture. The retroviral vector particles of the invention allow such rapid transduction to be performed.

One set of stem cells which form a particularly attractive target for gene therapy is the population of pluripotent hematopoietic stem cells that are chiefly found in the bone marrow, and, to a lesser extent, in the circulation. These cells are readily accessible by bone marrow aspiration or by peripheral blood cell harvesting, which may be followed by fractionation to isolate stem cells if relatively high concentrations of such cells are desired. Current methods for the transduction of bone marrow cells, and methods for the separation of various types of stem cells, are found in Strair et al., *Nucleic Acids Res.*, 18;4759–4762, 1990; Wilson, et al., *Proc. Natl. Acad. Sci.. U.S.A.*, 87:439–443;1990; U.S. Pat. No. 5,061,620; and PCT Patent Publications Nos. WO 91/18620, WO 93/18136, and WO 93/18137.

Once retroviral transduction of stem cells is accomplished in vitro, the treated cells can be reinfused intravenously, after which the stem cells will usually home to and develop in the bone marrow and produce mature blood cells. Since mature blood cells derived from stem cells circulate throughout the body, the genetically modified stem cells can effect the delivery of exogenous gene products to most tissues.

In addition to the foregoing advantages, many stem cells have the further advantage of possessing an almost unlimited capacity for self-renewal. Thus, using stem cells as the target cells for gene therapy can lead to long lasting, perhaps lifelong, delivery of a desired gene product.

Reviews of the advantages of using stem cells as target cells for gene therapy can be found in Boggs S. S., *Int. J. Cell Cloning*, 8.80–96; 1990; Kohn D. B., Anderson W. F., Blaese R. M., *Cancer Investigation*, 7:179–192;1989; Lehn P. M., *Bone Marrow Transplantation*, 5:287–293;1990, Verma I. M., *Scientific American*, pp. 68–84;1990; Weatherall D. J., *Nature*, 349:275–276; 1991; Felgner P. L., Rhodes G., *Nature*, 349:351–352; 1991.

In terms of clinical practice, the retroviral vector particles of the present invention are useful in the treatment of a broad range of inherited and acquired diseases and medical conditions including, without limitation, hematologic diseases, cardiopulmonary diseases, endocrinological diseases, transplantation associated disorders, autoimmune disorders, neurodegenerative diseases, neoplasias, and the like.

C. Administration

The retroviral vector particles of the invention can be used for ex vivo gene therapy in accordance with various techniques known in the art. In general terms, these techniques involve the removal of target cells of interest from a patient, incubation of the target cells with the retroviral vector particles, and reintroduction of the transduced target cells into the patient. Various procedures can be applied to the target cells while they are in the ex vivo state, including selection of subsets of the target cells prior to transduction, isolation of transduced cells, selection of subsets of isolated, transduced cells, propagation of target cells either before or after transduction, in cases where the cells are capable of proliferation, and the like.

Delivery of nucleic acid molecules of interest may also be accomplished in vivo by administration of the retroviral vector particles of the invention to a patient. In connection with such in vivo administration, the retroviral vector particles can be pre-treated in accordance with the procedures discussed in co-pending application Ser. No. 08/098,944, filed Jul. 28, 1993, in the name of James M. Mason and entitled "Pre-binding of Retroviral Vector Particles with Complement Components to Enable The Performance of Human Gene Therapy In Vivo." The administration can be performed locally, e.g., by aerosol, transmucosal, or transdermal delivery, or, more typically, by a systemic route, e.g., orally, intravenously, intraperitoneally, intramuscularly, transdermally, intradermally, subdermally, transmucosally, or intrathecally. For systemic administration, injection is preferred.

Intrathecal infusion into the cerebrospinal fluid in the central nervous system is a particularly preferred mode of delivery for gene therapy treatment of neurological disease by means of transduction of neuronal cells using the retroviral vector particles of the invention.

A variety of pharmaceutical formulations can be used for administration of the retroviral vector particles of the invention. Such formulations will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. See, for example, *Remington's Pharmaceutical Sciences*, Mack Publishing Company, Philadelphia, Pa., 17th ed., 1985.

The pharmaceutical compositions are suitable for use in a variety of drug delivery systems. Langer, *Science*, 249:1527–1533, 1990, reviews various drug delivery methods currently in use. In some cases, the drug delivery system will be designed to optimize the biodistribution and/or pharmacokinetics of the delivery of the retroviral vector particles. See, for example, *Remington's Pharmaceutical Sciences*, Supra, Chapters 37–39. For example, the particles can be incorporated in vesicles composed of substances such as proteins, lipids (for example, liposomes), carbohydrates, or synthetic polymers. See, for example, Langer, 1990, supra.

The pharmaceutical compositions of the invention can be administered in a variety of unit dosage forms. The dose will vary according to, e.g., the particular vector particle, the manner of administration, the particular disease being treated and its severity, the overall health and condition and age of the patient, and the judgment of the prescribing physician. Dosage levels for human subjects are generally between about $10^6$ and $10^{14}$ colony forming units of retroviral vector particles per patient per treatment.

Without intending to limit it in any manner, the present invention will be more fully described by the following examples.

EXAMPLE 1

Construction of Expression Vector pCPA-3

Figure 1:
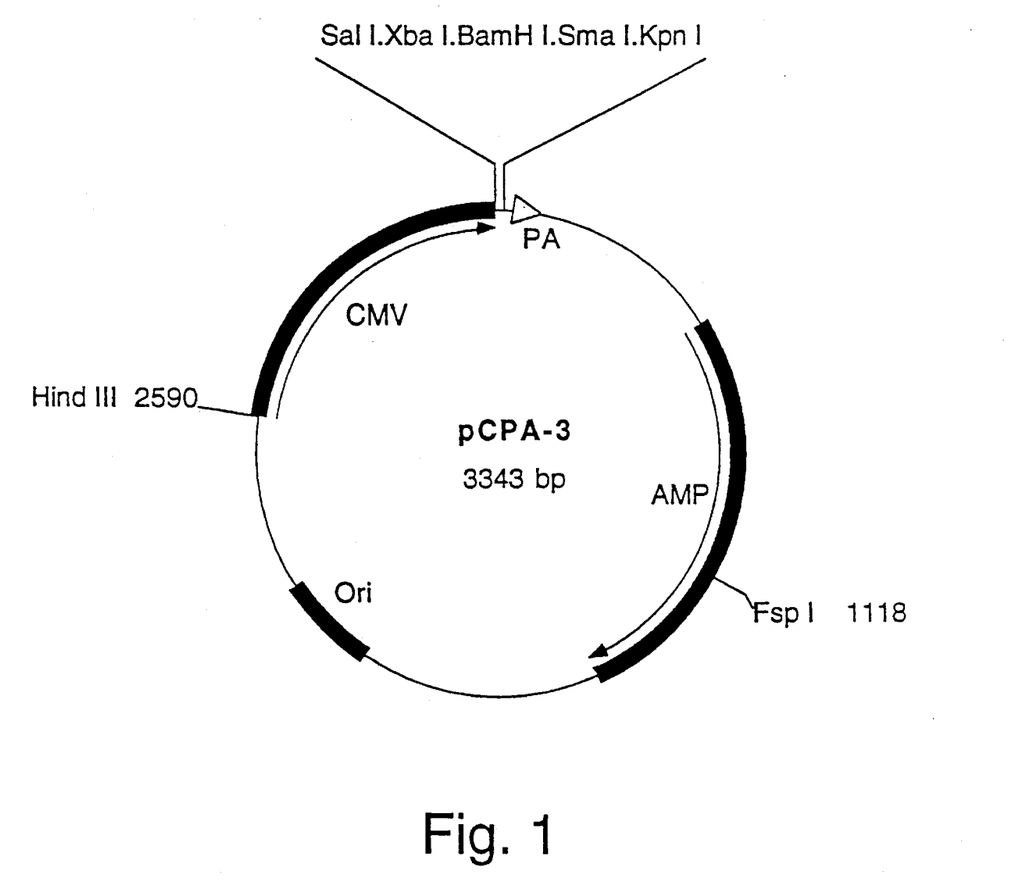
FIG. 1 is a map of plasmid vector pCPA-3. In this map, the polylinker cloning site, including restriction sites for SalI, XbaI, BamHI, SmaI, and KpnI, is located at the 12 o'clock position. Also indicated on the map is an open triangle representing the polyadenylation sequence from the SV40 large T antigen gene ("PA"), and solid bars representing the cytomegalovirus immediate early promoter/enhancer ("CMV"), a selectable marker—the ampicillin resistance conferring beta lactamase gene ("AMP"), and the colE1 bacterial origin of replication ("Ori").

Expression vector CPA-3, shown in FIG. 1, was constructed by combining fragments obtained from plasmid vector pUC19 (Yanisch-Peron, et al., Gene, 33:103–119, 1985) and plasmid vector pCee (Muenchau, et al., *Virology*, 186:161–166, 1992).

Specifically, both plasmids were separately digested with SacI, and the 171 bp fragment of pCee (containing the polyadenylation signal from the SV40 large T antigen gene) was isolated and ligated into the SacI linearized pUC19 to yield plasmid pUC19SVPA. In a separate reaction, pCee was digested with HindIII and SalI, and the 754 bp fragment containing the human cytomegalovirus (CMV) major immediate early promoter was isolated. This fragment was ligated into HindIII and SalI digested pUC19SVPA to yield plasmid vector CPA-2.

CPA-2 was digested with BsmI and NarI to excise a 247 bp fragment containing extraneous lacZ sequences, the cut ends were filled in, and the 3343 bp blunt ended fragment was self-ligated to produce plasmid vector pCPA-3.

EXAMPLE 2

Preparation of Packaging Vector pCA/NLS

Figure 2:
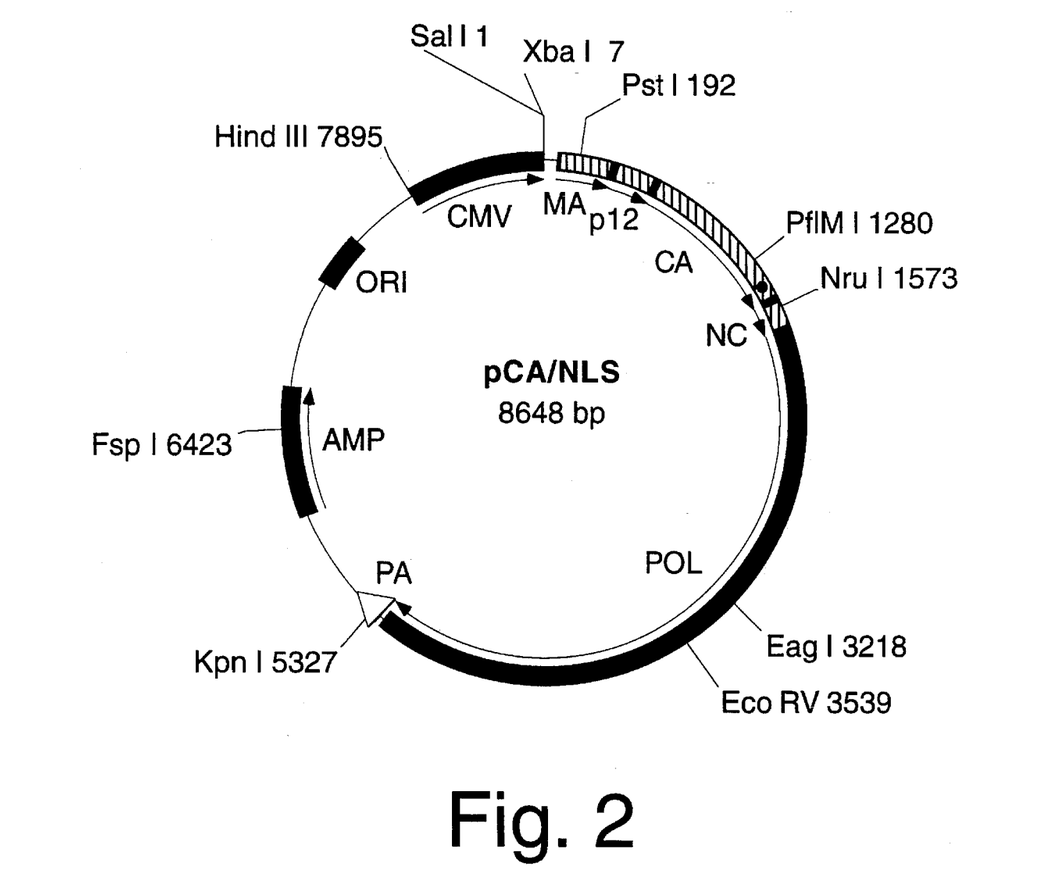
FIG. 2 is a map of packaging plasmid vector pCA/NLS. Indicated on this map is an open triangle representing the polyadenylation sequence from the SV40 large T antigen gene ("PA"), and solid bars representing the cytomegalovirus immediate early promoter/enhancer ("CMV"), a selectable marker—the ampicillin resistance conferring beta lactamase gene ("AMP"), the colE1 bacterial origin of replication ("ORI"), and the MoMLV pol. genes ("POL"). Shown as shaded bars separated by black stripes are the MoMLV gag genes MA (p15), p12, CA (p30), and NC (p10). The black dot in the shaded bar representing the gag CA gene indicates the location of the engineered NLS sequence of the invention, and the arrows indicate the direction of transcription for each gene.

This example illustrates the preparation of packaging vector pCA/NLS comprising a complete set of MoMLV gag and pol genes including a mutant gag CA gene which encodes an NLS sequence. The structure of this vector is shown in FIG. 2.

A. PCR Mutagenesis

Oligonucleotide primers were designed to: 1) produce amino acid changes creating a nuclear localization signal sequence situated within the carboxyl-terminal region of the gag capsid protein of MoMLV while maintaining the length of the native gag capsid protein, 2) facilitate the isolation of a fragment containing these mutations for subcloning, and 3) provide convenient restriction sites for the subcloning. These primers, referred to herein as the 31mer forward primer, the 17mer reverse primer, the 18mer forward primer, and the 129mer reverse primer, are listed in SEQ. ID NO:7, SEQ. ID NO:8, SEQ. ID NO:9, and SEQ. ID NO:10, respectively.

The 18mer forward primer and the 129mer reverse primer were used in a PCR reaction employing plasmid 3PO of PCT Patent Publication No. WO 89/07150 as the template. This reaction generated an approximately 299 base pair fragment. Upon digestion with PflMI and NruI, the fragment yielded three sub-fragments, only one of which was large enough to be resolved using conventional agarose gel electrophoresis. That fragment included 289 base pairs of double stranded DNA with three unpaired bases at one end (referred to hereinafter as the "292 nt fragment"). SEQ. ID NO:11 shows the 292 nt fragment.

B. Subcloning

The 31mer forward primer and the 17mer reverse primer are used in a PCR reaction employing plasmid 3PO as the template. This reaction generates an approximately 198 base pair fragment. Upon digestion with XbaI and PstI, the fragment yields three sub-fragments, only one of which is large enough to be resolved using conventional agarose gel electrophoresis. That fragment includes 181 base pairs of double stranded DNA flanked with four unpaired bases at each end (referred to hereinafter as the "189 nt fragment").

The 189 nt fragment is subcloned into the plasmid vector, Bluescript 2 KS+, Stratagene Cloning Systems, San Diego, Calif., as an insert fragment, and that insert is sequenced to confirm that the desired nucleotide sequence, i.e., SEQ. ID NO:12, is obtained.

The 189 nt fragment does not contain the entire gag matrix-encoding sequence, nor does it contain the other gag genes or the pol genes located downstream of the gag MA gene in the MoMLV genome. The remainder of these gag and pol sequences from the MoMLV genome are provided as the 292 nt fragment and a set of small (on the order of less than about 4 kbp) restriction fragments obtained from plasmid 3PO.

In a series of subcloning steps, the 292 nt fragment and the members of the set of small restriction fragments are sequentially ligated into the polylinker cloning site of expression vector CPA-3 (see Example 1) together with the 189 nt fragment starting with the PstI site of the 189 nt fragment. After each subcloning step, plasmids are amplified by growth in host bacteria. In general, restriction mapping is undertaken after each subcloning step to confirm that the desired construction is obtained. Plasmids containing the desired partial construction serve as recipients of further fragment insertions until the complete assemblage of the gag and pol genes in their native order has been obtained. This completed assemblage comprises the pCA/NLS packaging vector of FIG. 2. As a result of using the 292 nt fragment, this vector encodes an oncoretroviral gag capsid protein which has been mutated so as to contain a nuclear localization signal sequence.

EXAMPLE 3

Preparation of Packaging Cells

The pCA/NLS packaging vector of Example 2 is cotransfected into NIH/3T3 cells (ATCC # CRL 1658) with plasmid pTH directing the expression of the hygromycin resistance gene Hph. Plasmid pTH was derived from plasmid p291 (Yates, et al., *Nature*, 313:811–815, 1985) by digestion of p291 with EcoRV and SspI, purification of the resulting Hph containing fragment, and self ligation of the purified fragment. The transfected NIH/3T3 cells are grown in DMEM supplemented with 10% heat inactivated FBS in the presence of at least 100 µg/ml of hygromycin B.

Resistant colonies surviving after 7–14 days are screened for the expression of reverse transcriptase (RT) using the method of Markowitz, et al., 1988, supra. RT expressing cells are then co-transfected with packaging vector pCAE (Morgan, et al., *J. Virol*, 67:4712–4721, 1993), which contains an env gene which codes for an amphotropic envelope protein, and with plasmid pCPURO.

Figure 3:
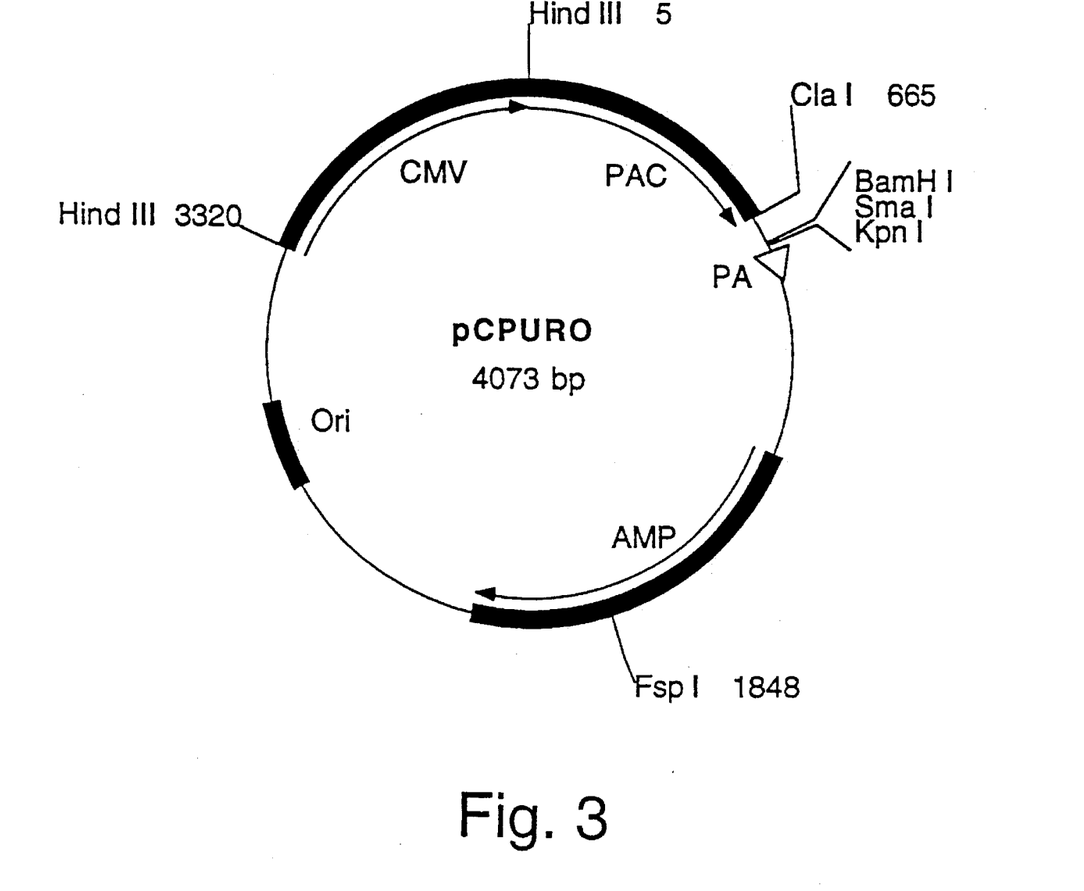
FIG. 3 is a map of plasmid vector pCPURO. Indicated on this map is an open triangle representing the polyadenylation sequence from the SV40 large T antigen gene ("PA"), and solid bars representing the cytomegalovirus immediate early promoter/enhancer ("CMV"), a selectable marker—the ampicillin resistance conferring beta lactamase gene ("AMP"), the colE1 bacterial origin of replication ("Ori"), and the puromycin resistance gene Pac ("PAC"). The arrows indicate the direction of transcription for each gene.

Plasmid pCPURO is a ligation product of the pCPA-3 vector and a restriction fragment obtained from the pBabepuro vector (Morgenstern and Land, 1990 supra). The pBabepuro vector is digested with HindIII and the resulting ends of the linearized plasmid are filled in. The linearized plasmid is then digested with NheI and an approximately 730 bp fragment containing the puromycin resistance gene, paC, is isolated. The pCPA-3 vector is digested with SalI, and the resulting ends of the linearized plasmid are filled in. The linearized pCPA-3 is then digested with XbaI, and the resulting approximately 3300 bp fragment is ligated to the approximately 730 bp fragment containing the puromycin resistance gene to produce pCPURO (see FIG. 3).

The co-transfected cells are grown in DMEM supplemented with 10% heat inactivated FBS in the presence of at least 0.5 µg/ml of puromycin for 7–14 days. Candidate packaging cell lines are identified as those puromycin resistant colonies/groups of colonies, which express amphotropic envelope protein. Cells expressing amphotropic envelope protein are isolated by multiple rounds of antibody labelling and FACS sorting followed by isolation of individual clones. Antibody labelling is accomplished by incubating with rat monoclonal antibody 83A25 which labels the amphotropic envelope protein (Evans, et al., *J. Virol.*, 64:6176–6183, 1990) as described in Kadan, et al., *J. Virol.*, 66:2281–2287, 1992, but using an FITC-conjugated goat anti-rat secondary antibody instead of the secondary antibody used by Kadan et al.

The candidate packaging cells expressing the highest levels of amphotropic envelope protein are then grown as candidate packaging cell lines which are then tested for their ability to package retroviral vectors. Specifically, retroviral vector LXSN is introduced into cells of the candidate packaging line using the method of Miller and Rosman, 1989, supra. The LXSN vector comprises a ψ packaging signal and a neomycin phosphotransferase gene conferring resistance to the neomycin analog G418 (Miller and Rosman, supra).

The LXSN-transfected cells are incubated for at least 24 hours in DMEM supplemented with 10% heat inactivated FBS, after which time the culture medium is changed and the cells are incubated for at least another 8 hours. Supernatant medium is then collected, filtered, and used to transduce untransfected NIH/3T3 cells. These NIH/3T3 cells are subsequently incubated for at least 8 days in DMEM supplemented with 10% heat inactivated FBS in the presence of at least 300 μg/ml of active G418.

Those candidate packaging cell lines which yield LXSN-transfected producer cells which generate supernatants that transduce NIH/3T3 cells and thus enable their survival in the presence of G418 are the packaging cell lines of the invention. Based on the foregoing, these packaging cells express an oncoretroviral gag capsid protein which has been mutated so as to contain a nuclear localization signal sequence. The packaging cell lines that generate cells that produce supernatants yielding the highest numbers of surviving transduced NIH/3T3 cells are further cultured and are transfected with retroviral vectors of interest to form producer cells.

EXAMPLE 4

Transduction of Non-Proliferating Cells By Retroviral Vector Particles Comprising a gag Protein Containing an NLS Sequence The packaging cells of Example 3 are transfected with the retroviral vector pLZ12 (Galileo et al. PNAS, 87:458–462, 1990) which encodes a bacterial beta-galactosidase enzyme which has been mutated to include an NLS sequence so that the enzyme, if produced in a target cell, is localized in the nucleus of that cell. In this way, a highly sensitive readout of those cells which are successfully transduced is achieved, i.e., the successfully transduced cells have colored nuclei when the appropriate substrate is supplied to the cells.

The producer cells resulting from this transfection are cultured and used to prepare supernatants containing pLZ12 retroviral vector particles. In accordance with the construction of the packaging cells described above, these retroviral vector particles contain an oncoretroviral gag capsid protein which has been mutated so as to contain a nuclear localization signal sequence.

The retroviral vector particles are administered to PC12 cells (ATCC CRL 1721) which have been pre-treated with nerve growth factor (NGF) in medium containing low (1%) serum to block proliferation in accordance with the methods disclosed in Greene et al., "Methodologies for the Culture and Experimental Use of the PC12 Rat Pheochromocytoma Cell Line", in *Culturing Nerve Cells*, edited by G. Banker and K. Goslin, MIT Press, Chapter 9, pages 207–226 and 413–448, 1991. As disclosed therein, PC12 cells treated in this manner differentiate and develop a neuronal phenotype. As controls, pLZ12 retroviral vector particles prepared using pLZ12 transfected PA317 packaging cells (ATCC CRL 9078), which particles do not include an NLS sequence in any of their gag proteins (hereinafter referred to as the "control retroviral vector particles"), are also administered to the non-dividing PC12 cells.

After incubation for 6–24 hours, the two sets of cells are assayed for expression of beta-galactosidase as described in Galileo et al., supra. Substantial expression of beta-galactosidase activity is detected in the non-proliferating cells when the retroviral vector particles of the invention are used, but not when the control retroviral vector particles are used.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

Although preferred and other embodiments of the invention have been described herein, other embodiments may be perceived by those skilled in the art without departing from the scope of the invention as defined by the following claims.

---

What is claimed is:

1. A retroviral vector particle comprising an oncoretroviral gag protein which has been mutated so as to contain a nuclear localization signal sequence, wherein the gag protein is a gag capsid protein.

2. A retroviral packaging cell expressing an oncoretroviral gag protein which has been mutated so as to contain a nuclear localization signal sequence, wherein the gag protein is a gag capsid protein.

3. A nucleic acid molecule encoding an oncoretroviral gag protein which has been mutated so as to contain a nuclear localization signal sequence, wherein the gag protein is a gag capsid protein.

4. A method for introducing an exogenous gene into a target cell comprising:

(a) providing a retroviral packaging cell expressing an oncoretroviral gag protein which has been mutated so as to contain a nuclear localization signal sequence, wherein the gag protein is a gag capsid protein;

(b) introducing a retroviral vector containing said exogenous gene into the packaging cell;

(c) incubating the packaging cell of step (b) under conditions wherein retroviral vector particles are produced; and (d) transducing the target cell with the retroviral vector particles of step (c).

5. The method of claim 4 wherein the target cell is a non-dividing cell.

6. The method of claim 4 wherein the target cell is a stem cell.

7. The method of claim 4 wherein the target cell is a neuronal cell.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 7 amino acid residues
        ( B ) TYPE: amino acid
        ( D ) TOPOLOGY: linear     ( v i ) ORIGINAL SOURCE:
        ( A ) ORGANISM: Simian Virus 40

( x ) PUBLICATION INFORMATION:
        ( A ) AUTHORS: Kalderon, D, Roberts, BL,
            Richardson, WD, Smith, AE
        ( B ) JOURNAL: Cell
        ( C ) VOLUME: 39
        ( F ) PAGES: 499-509
        ( G ) DATE: DEC-1984

( x i ) SEQUENCE DESCRIPTION: SEQ ID NO:1:

Pro Lys Lys Lys Arg Lys Val
                5

( 2 ) INFORMATION FOR SEQ ID NO:2:

( i ) SEQUENCE CHARACTERISTICS:
        ( A ) LENGTH: 20 amino acid residues
        ( B ) TYPE: amino acid
        ( D ) TOPOLOGY: linear     ( v i ) ORIGINAL SOURCE:
        ( A ) ORGANISM: Xenopus laevis     ( x ) PUBLICATION INFORMATION:
        ( A ) AUTHORS: Dingwall, C, Robbins, J,
            Dilworth, SM, Roberts, B,
            Richardson, WD
        ( B ) JOURNAL: Journal of Cell Biology
        ( C ) VOLUME: 107
        ( F ) PAGES: 841-849
        ( G ) DATE: SEP-1988

( x i ) SEQUENCE DESCRIPTION: SEQ ID NO:2:

Ala Val Lys Arg Pro Ala Ala Thr Lys Lys
                5                       10

Ala Gly Gln Ala Lys Lys Lys Lys Leu Asp
                15                      20

( 2 ) INFORMATION FOR SEQ ID NO:3:

( i ) SEQUENCE CHARACTERISTICS:
        ( A ) LENGTH: 789 base pairs
        ( B ) TYPE: Nucleic Acid
        ( C ) STRANDEDNESS: Double
        ( D ) TOPOLOGY: Linear     ( i i ) MOLECULE TYPE: cDNA to genomic RNA     ( i i i ) HYPOTHETICAL: No     ( i v ) ANTI-SENSE: No     ( v i ) ORIGINAL SOURCE:
        ( A ) ORGANISM: Moloney Murine Leukemia Virus     ( x ) PUBLICATION INFORMATION:
        ( A ) AUTHORS: Shinnick, TM, Lerner, RA,
            Sutcliffe, JG
        ( B ) JOURNAL: Nature
        ( C ) VOLUME: 293
        ( F ) PAGES: 543-548
        ( G ) DATE: 15-OCT-1984

( x i ) SEQUENCE DESCRIPTION: SEQ ID NO:3:

```
CCC  CTC  CGC  GCA  GGA  GGA  AAC  GGA  CAG  CTT                    30
Pro  Leu  Arg  Ala  Gly  Gly  Asn  Gly  Gln  Leu
               5                             10

CAA  TAC  TGG  CCG  TTC  TCC  TCT  TCT  GAC  CTT                    60
Gln  Tyr  Trp  Pro  Phe  Ser  Ser  Ser  Asp  Leu
               15                            20

TAC  AAC  TGG  AAA  AAT  AAT  AAC  CCT  TCT  TTT                    90
Tyr  Asn  Trp  Lys  Asn  Asn  Asn  Pro  Ser  Phe
               25                            30

TCT  GAA  GAT  CCA  GGT  AAA  CTG  ACA  GCT  CTG                    120
Ser  Glu  Asp  Pro  Gly  Lys  Leu  Thr  Ala  Leu
               35                            40

ATC  GAG  TCT  GTT  CTC  ATC  ACC  CAT  CAG  CCC                    150
Ile  Glu  Ser  Val  Leu  Ile  Thr  His  Gln  Pro
               45                            50
```

| | | | | | | | | | | |
|---|---|---|---|---|---|---|---|---|---|---|
| ACC | TGG | GAC | GAC | TGT | CAG | CAG | CTG | TTG | GGG | 180 |
| Thr | Trp | Asp | Asp | Cys | Gln | Gln | Leu | Leu | Gly | |
| | | | 55 | | | | | | 60 | |
| ACT | CTG | CTG | ACC | GGA | GAA | GAA | AAA | CAA | CGG | 210 |
| Thr | Leu | Leu | Thr | Gly | Glu | Glu | Lys | Gln | Arg | |
| | | | 65 | | | | | | 70 | |
| GTG | CTC | TTA | GAG | GCT | AGA | AAG | GCG | GTG | CGG | 240 |
| Val | Leu | Leu | Glu | Ala | Arg | Lys | Ala | Val | Arg | |
| | | | 75 | | | | | | 80 | |
| GGC | GAT | GAT | GGG | CGC | CCC | ACT | CAA | CTG | CCC | 270 |
| Gly | Asp | Asp | Gly | Arg | Pro | Thr | Gln | Leu | Pro | |
| | | | 85 | | | | | | 90 | |
| AAT | GAA | GTC | GAT | GCC | GCT | TTT | CCC | CTC | GAG | 300 |
| Asn | Glu | Val | Asp | Ala | Ala | Phe | Pro | Leu | Glu | |
| | | | 95 | | | | | | 100 | |
| CGC | CCA | GAC | TGG | GAT | TAC | ACC | ACC | CAG | GCA | 330 |
| Arg | Pro | Asp | Trp | Asp | Tyr | Thr | Thr | Gln | Ala | |
| | | | 105 | | | | | | 110 | |
| GGT | AGG | AAC | CAC | CTA | GTC | CAC | TAT | CGC | CAG | 360 |
| Gly | Arg | Asn | His | Leu | Val | His | Tyr | Arg | Gln | |
| | | | 115 | | | | | | 120 | |
| TTG | CTC | CTA | GCG | GGT | CTC | CAA | AAC | GCG | GGC | 390 |
| Leu | Leu | Leu | Ala | Gly | Leu | Gln | Asn | Ala | Gly | |
| | | | 125 | | | | | | 130 | |
| AGA | AGC | CCC | ACC | AAT | TTG | GCC | AAG | GTA | AAA | 420 |
| Arg | Ser | Pro | Thr | Asn | Leu | Ala | Lys | Val | Lys | |
| | | | 135 | | | | | | 140 | |
| GGA | ATA | ACA | CAA | GGG | CCC | AAT | GAG | TCT | CCC | 450 |
| Gly | Ile | Thr | Gln | Gly | Pro | Asn | Glu | Ser | Pro | |
| | | | 145 | | | | | | 150 | |
| TCG | GCC | TTC | CTA | GAG | AGA | CTT | AAG | GAA | GCC | 480 |
| Ser | Ala | Phe | Leu | Glu | Arg | Leu | Lys | Glu | Ala | |
| | | | 155 | | | | | | 160 | |
| TAT | CGC | AGG | TAC | ACT | CCT | TAT | GAC | CCT | GAG | 510 |
| Tyr | Arg | Arg | Tyr | Thr | Pro | Tyr | Asp | Pro | Glu | |
| | | | 165 | | | | | | 170 | |
| GAC | CCA | GGG | CAA | GAA | ACT | AAT | GTG | TCT | ATG | 540 |
| Asp | Pro | Gly | Gln | Glu | Thr | Asn | Val | Ser | Met | |
| | | | 175 | | | | | | 180 | |
| TCT | TTC | ATT | TGG | CAG | TCT | GCC | CCA | GAC | ATT | 570 |
| Ser | Phe | Ile | Trp | Gln | Ser | Ala | Pro | Asp | Ile | |
| | | | 185 | | | | | | 190 | |
| GGG | AGA | AAG | TTA | GAG | AGG | TTA | GAA | GAT | TTA | 600 |
| Gly | Arg | Lys | Leu | Glu | Arg | Leu | Glu | Asp | Leu | |
| | | | 195 | | | | | | 200 | |
| AAA | AAC | AAG | ACG | CTT | GGA | GAT | TTG | GTT | AGA | 630 |
| Lys | Asn | Lys | Thr | Leu | Gly | Asp | Leu | Val | Arg | |
| | | | 205 | | | | | | 210 | |
| GAG | GCA | GAA | AAG | ATC | TTT | AAT | AAA | CGA | GAA | 660 |
| Glu | Ala | Glu | Lys | Ile | Phe | Asn | Lys | Arg | Glu | |
| | | | 215 | | | | | | 220 | |
| ACC | CCG | GAA | GAA | AGA | GAG | GAA | CGT | ATC | AGG | 690 |
| Thr | Pro | Glu | Glu | Arg | Glu | Glu | Arg | Ile | Arg | |
| | | | 225 | | | | | | 230 | |
| AGA | GAA | ACA | GAG | GAA | AAA | GAA | GAA | CGC | CGT | 720 |
| Arg | Glu | Thr | Glu | Glu | Lys | Glu | Glu | Arg | Arg | |
| | | | 235 | | | | | | 240 | |
| AGG | ACA | GAG | GAT | GAG | CAG | AAA | GAG | AAA | GAA | 750 |
| Arg | Thr | Glu | Asp | Glu | Gln | Lys | Glu | Lys | Glu | |
| | | | 245 | | | | | | 250 | |

| | | | | | | | | | |
|---|---|---|---|---|---|---|---|---|---|
| AGA | GAT | CGT | AGG | AGA | CAT | AGA | GAG | ATG | AGC |
| Arg | Asp | Arg | Arg | Arg | His | Arg | Glu | Met | Ser |
| | | | | 255 | | | | 260 | |

780

| | | |
|---|---|---|
| AAG | CTA | TTG |
| Lys | Leu | Leu |

789

( 2 ) INFORMATION FOR SEQ ID NO:4:

( i ) SEQUENCE CHARACTERISTICS:
        ( A ) LENGTH: 6 amino acid residues
        ( B ) TYPE: amino acid
        ( D ) TOPOLOGY: linear     ( v i ) ORIGINAL SOURCE:
        ( A ) ORGANISM: Simian Virus 40

( x ) PUBLICATION INFORMATION:
        ( A ) AUTHORS: Kalderon, D, Roberts, BL,
            Richardson, WD, Smith, AE
        ( B ) JOURNAL: Cell
        ( C ) VOLUME: 39
        ( F ) PAGES: 499-509
        ( G ) DATE: DEC-1984

( x i ) SEQUENCE DESCRIPTION: SEQ ID NO:4:

Lys  Lys  Lys  Arg  Lys  Val
                        5

( 2 ) INFORMATION FOR SEQ ID NO:5:

( i ) SEQUENCE CHARACTERISTICS:
        ( A ) LENGTH: 789 base pairs
        ( B ) TYPE: Nucleic Acid
        ( C ) STRANDEDNESS: Double
        ( D ) TOPOLOGY: linear     ( i v ) ANTI-SENSE: No     ( x i ) SEQUENCE DESCRIPTION: SEQ ID NO:5:

| | | | | | | | | | |
|---|---|---|---|---|---|---|---|---|---|
| CCC | CTC | CGC | GCA | GGA | GGA | AAC | GGA | CAG | CTT |
| Pro | Leu | Arg | Ala | Gly | Gly | Asn | Gly | Gln | Leu |
| | | | | 5 | | | | | 10 |

30

| | | | | | | | | | |
|---|---|---|---|---|---|---|---|---|---|
| CAA | TAC | TGG | CCG | TTC | TCC | TCT | TCT | GAC | CTT |
| Gln | Tyr | Trp | Pro | Phe | Ser | Ser | Ser | Asp | Leu |
| | | | | 15 | | | | | 20 |

60

| | | | | | | | | | |
|---|---|---|---|---|---|---|---|---|---|
| TAC | AAC | TGG | AAA | AAT | AAT | AAC | CCT | TCT | TTT |
| Tyr | Asn | Trp | Lys | Asn | Asn | Asn | Pro | Ser | Phe |
| | | | | 25 | | | | | 30 |

90

| | | | | | | | | | |
|---|---|---|---|---|---|---|---|---|---|
| TCT | GAA | GAT | CCA | GGT | AAA | CTG | ACA | GCT | CTG |
| Ser | Glu | Asp | Pro | Gly | Lys | Leu | Thr | Ala | Leu |
| | | | | 35 | | | | | 40 |

120

| | | | | | | | | | |
|---|---|---|---|---|---|---|---|---|---|
| ATC | GAG | TCT | GTT | CTC | ATC | ACC | CAT | CAG | CCC |
| Ile | Glu | Ser | Val | Leu | Ile | Thr | His | Gln | Pro |
| | | | | 45 | | | | | 50 |

150

| | | | | | | | | | |
|---|---|---|---|---|---|---|---|---|---|
| ACC | TGG | GAC | GAC | TGT | CAG | CAG | CTG | TTG | GGG |
| Thr | Trp | Asp | Asp | Cys | Gln | Gln | Leu | Leu | Gly |
| | | | | 55 | | | | | 60 |

180

| | | | | | | | | | |
|---|---|---|---|---|---|---|---|---|---|
| ACT | CTG | CTG | ACC | GGA | GAA | GAA | AAA | CAA | CGG |
| Thr | Leu | Leu | Thr | Gly | Glu | Glu | Lys | Gln | Arg |
| | | | | 65 | | | | | 70 |

210

| | | | | | | | | | |
|---|---|---|---|---|---|---|---|---|---|
| GTG | CTC | TTA | GAG | GCT | AGA | AAG | GCG | GTG | CGG |
| Val | Leu | Leu | Glu | Ala | Arg | Lys | Ala | Val | Arg |
| | | | | 75 | | | | | 80 |

240

| | | | | | | | | | |
|---|---|---|---|---|---|---|---|---|---|
| GGC | GAT | GAT | GGG | CGC | CCC | ACT | CAA | CTG | CCC |
| Gly | Asp | Asp | Gly | Arg | Pro | Thr | Gln | Leu | Pro |
| | | | | 85 | | | | | 90 |

270

```
AAT  GAA  GTC  GAT  GCC  GCT  TTT  CCC  CTC  GAG                    300
Asn  Glu  Val  Asp  Ala  Ala  Phe  Pro  Leu  Glu
               95                           100

CGC  CCA  GAC  TGG  GAT  TAC  ACC  ACC  CAG  GCA                    330
Arg  Pro  Asp  Trp  Asp  Tyr  Thr  Thr  Gln  Ala
               105                          110

GGT  AGG  AAC  CAC  CTA  GTC  CAC  TAT  CGC  CAG                    360
Gly  Arg  Asn  His  Leu  Val  His  Tyr  Arg  Gln
               115                          120

TTG  CTC  CTA  GCG  GGT  CTC  CAA  AAC  GCG  GGC                    390
Leu  Leu  Leu  Ala  Gly  Leu  Gln  Asn  Ala  Gly
               125                          130

AGA  AGC  CCC  ACC  AAT  TTG  GCC  AAG  GTA  AAA                    420
Arg  Ser  Pro  Thr  Asn  Leu  Ala  Lys  Val  Lys
               135                          140

GGA  ATA  ACA  CAA  GGG  CCC  AAT  GAG  TCT  CCC                    450
Gly  Ile  Thr  Gln  Gly  Pro  Asn  Glu  Ser  Pro
               145                          150

TCG  GCC  TTC  CTA  GAG  AGA  CTT  AAG  GAA  GCC                    480
Ser  Ala  Phe  Leu  Glu  Arg  Leu  Lys  Glu  Ala
               155                          160

TAT  CGC  AGG  TAC  ACT  CCT  TAT  GAC  CCT  GAG                    510
Tyr  Arg  Arg  Tyr  Thr  Pro  Tyr  Asp  Pro  Glu
               165                          170

GAC  CCA  GGG  CAA  GAA  ACT  AAT  GTG  TCT  ATG                    540
Asp  Pro  Gly  Gln  Glu  Thr  Asn  Val  Ser  Met
               175                          180

TCT  TTC  ATT  TGG  CAG  TCT  GCC  CCA  GAC  ATT                    570
Ser  Phe  Ile  Trp  Gln  Ser  Ala  Pro  Asp  Ile
               185                          190

GGG  AGA  AAG  TTA  GAG  AGG  TTA  GAA  GAT  TTA                    600
Gly  Arg  Lys  Leu  Glu  Arg  Leu  Glu  Asp  Leu
               195                          200

AAA  AAC  AAG  ACG  CTT  GGA  GAT  TTG  GTT  AGA                    630
Lys  Asn  Lys  Thr  Leu  Gly  Asp  Leu  Val  Arg
               205                          210

GAG  GCA  GAA  AAG  ATC  TTT  AAT  AAA  CGA  GAA                    660
Glu  Ala  Glu  Lys  Ile  Phe  Asn  Lys  Arg  Glu
               215                          220

ACC  CCG  GAA  GAA  AGA  GAG  GAA  CGT  ATC  AGG                    690
Thr  Pro  Glu  Glu  Arg  Glu  Glu  Arg  Ile  Arg
               225                          230

AGA  GAA  ACA  GAG  GAA  AAA  GAA  GAA  CGC  CGT                    720
Arg  Glu  Thr  Glu  Glu  Lys  Glu  Glu  Arg  Arg
               235                          240

AGG  ACA  GAG  GAT  GAG  CAG  AAA  GAG  AAA  GAA                    750
Arg  Thr  Glu  Asp  Glu  Gln  Lys  Glu  Lys  Glu
               245                          250

AGA  CCT  AAG  AAG  AAA  CGT  AAA  GTG  ATG  AGC                    780
Arg  Pro  Lys  Lys  Lys  Arg  Lys  Val  Met  Ser
               255                          260

AAG  CTA  TTG                                                       789
Lys  Leu  Leu
```

( 2 ) INFORMATION FOR SEQ ID NO:6:

( i ) SEQUENCE CHARACTERISTICS:
        ( A ) LENGTH: 789 base pairs
        ( B ) TYPE: Nucleic Acid
        ( C ) STRANDEDNESS: Double
        ( D ) TOPOLOGY: linear ( x i ) SEQUENCE DESCRIPTION: SEQ ID NO:6:

| | | | | | | | | | |
|---|---|---|---|---|---|---|---|---|---|
| CCC | CTC | CGC | GCA | GGA | GGA | AAC | GGA | CAG | CTT | 30 |
| Pro | Leu | Arg | Ala | Gly | Gly | Asn | Gly | Gln | Leu |
| | | | | 5 | | | | | 10 |
| CAA | TAC | TGG | CCG | TTC | TCC | TCT | TCT | GAC | CTT | 60 |
| Gln | Tyr | Trp | Pro | Phe | Ser | Ser | Ser | Asp | Leu |
| | | | | 15 | | | | | 20 |
| TAC | AAC | TGG | AAA | AAT | AAT | AAC | CCT | TCT | TTT | 90 |
| Tyr | Asn | Trp | Lys | Asn | Asn | Asn | Pro | Ser | Phe |
| | | | | 25 | | | | | 30 |
| TCT | GAA | GAT | CCA | GGT | AAA | CTG | ACA | GCT | CTG | 120 |
| Ser | Glu | Asp | Pro | Gly | Lys | Leu | Thr | Ala | Leu |
| | | | | 35 | | | | | 40 |
| ATC | GAG | TCT | GTT | CTC | ATC | ACC | CAT | CAG | CCC | 150 |
| Ile | Glu | Ser | Val | Leu | Ile | Thr | His | Gln | Pro |
| | | | | 45 | | | | | 50 |
| ACC | TGG | GAC | GAC | TGT | CAG | CAG | CTG | TTG | GGG | 180 |
| Thr | Trp | Asp | Asp | Cys | Gln | Gln | Leu | Leu | Gly |
| | | | | 55 | | | | | 60 |
| ACT | CTG | CTG | ACC | GGA | GAA | GAA | AAA | CAA | CGG | 210 |
| Thr | Leu | Leu | Thr | Gly | Glu | Glu | Lys | Gln | Arg |
| | | | | 65 | | | | | 70 |
| GTG | CTC | TTA | GAG | GCT | AGA | AAG | GCG | GTG | CGG | 240 |
| Val | Leu | Leu | Glu | Ala | Arg | Lys | Ala | Val | Arg |
| | | | | 75 | | | | | 80 |
| GGC | GAT | GAT | GGG | CGC | CCC | ACT | CAA | CTG | CCC | 270 |
| Gly | Asp | Asp | Gly | Arg | Pro | Thr | Gln | Leu | Pro |
| | | | | 85 | | | | | 90 |
| AAT | GAA | GTC | GAT | GCC | GCT | TTT | CCC | CTC | GAG | 300 |
| Asn | Glu | Val | Asp | Ala | Ala | Phe | Pro | Leu | Glu |
| | | | | 95 | | | | | 100 |
| CGC | CCA | GAC | TGG | GAT | TAC | ACC | ACC | CAG | GCA | 330 |
| Arg | Pro | Asp | Trp | Asp | Tyr | Thr | Thr | Gln | Ala |
| | | | | 105 | | | | | 110 |
| GGT | AGG | AAC | CAC | CTA | GTC | CAC | TAT | CGC | CAG | 360 |
| Gly | Arg | Asn | His | Leu | Val | His | Tyr | Arg | Gln |
| | | | | 115 | | | | | 120 |
| TTG | CTC | CTA | GCG | GGT | CTC | CAA | AAC | GCG | GGC | 390 |
| Leu | Leu | Leu | Ala | Gly | Leu | Gln | Asn | Ala | Gly |
| | | | | 125 | | | | | 130 |
| AGA | AGC | CCC | ACC | AAT | TTG | GCC | AAG | GTA | AAA | 420 |
| Arg | Ser | Pro | Thr | Asn | Leu | Ala | Lys | Val | Lys |
| | | | | 135 | | | | | 140 |
| GGA | ATA | ACA | CAA | GGG | CCC | AAT | GAG | TCT | CCC | 450 |
| Gly | Ile | Thr | Gln | Gly | Pro | Asn | Glu | Ser | Pro |
| | | | | 145 | | | | | 150 |
| TCG | GCC | TTC | CTA | GAG | AGA | CTT | AAG | GAA | GCC | 480 |
| Ser | Ala | Phe | Leu | Glu | Arg | Leu | Lys | Glu | Ala |
| | | | | 155 | | | | | 160 |
| TAT | CGC | AGG | TAC | ACT | CCT | TAT | GAC | CCT | GAG | 510 |
| Tyr | Arg | Arg | Tyr | Thr | Pro | Tyr | Asp | Pro | Glu |
| | | | | 165 | | | | | 170 |
| GAC | CCA | GGG | CAA | GAA | ACT | AAT | GTG | TCT | ATG | 540 |
| Asp | Pro | Gly | Gln | Glu | Thr | Asn | Val | Ser | Met |
| | | | | 175 | | | | | 180 |
| TCT | TTC | ATT | TGG | CAG | TCT | GCC | CCA | GAC | ATT | 570 |
| Ser | Phe | Ile | Trp | Gln | Ser | Ala | Pro | Asp | Ile |
| | | | | 185 | | | | | 190 |
| GGG | AGA | AAG | TTA | GAG | AGG | TTA | GAA | GAT | TTA | 600 |
| Gly | Arg | Lys | Leu | Glu | Arg | Leu | Glu | Asp | Leu |

|   |   |   |   |   |   |   |   |   |   |
|---|---|---|---|---|---|---|---|---|---|
|   |   |   | 195 |   |   |   | 200 |   |   |
| AAA | AAC | AAG | ACG | CTT | GGA | GAT | TTG | GTT | AGA | 630 |
| Lys | Asn | Lys | Thr | Leu | Gly | Asp | Leu | Val | Arg |   |
|   |   |   | 205 |   |   |   |   |   | 210 |   |
| GAG | GCA | GAA | AAG | ATC | TTT | AAT | AAA | CGA | GAA | 660 |
| Glu | Ala | Glu | Lys | Ile | Phe | Asn | Lys | Arg | Glu |   |
|   |   |   |   | 215 |   |   |   |   | 220 |   |
| ACC | CCG | GAA | GAA | AGA | GAG | GAA | CGT | ATC | AGG | 690 |
| Thr | Pro | Glu | Glu | Arg | Glu | Glu | Arg | Ile | Arg |   |
|   |   |   |   | 225 |   |   |   |   | 230 |   |
| AGA | GAA | ACA | GAG | GAA | AAA | GAA | GAA | CGC | CGT | 720 |
| Arg | Glu | Thr | Glu | Glu | Lys | Glu | Glu | Arg | Arg |   |
|   |   |   |   | 235 |   |   |   |   | 240 |   |
| AGG | ACA | GAG | GAT | GAG | CAG | AAA | GAG | AAA | GAA | 750 |
| Arg | Thr | Glu | Asp | Glu | Gln | Lys | Glu | Lys | Glu |   |
|   |   |   |   | 245 |   |   |   |   | 250 |   |
| AGA | GAT | AAG | AAG | AAA | CGT | AAA | GTG | ATG | AGC | 780 |
| Arg | Asp | Lys | Lys | Lys | Arg | Lys | Val | Met | Ser |   |
|   |   |   |   | 255 |   |   |   |   | 260 |   |
| AAG | CTA | TTG |   |   |   |   |   |   |   | 789 |
| Lys | Leu | Leu |   |   |   |   |   |   |   |   |

( 2 ) INFORMATION FOR SEQ ID NO:7:

( i ) SEQUENCE CHARACTERISTICS:
        ( A ) LENGTH: 31 bases
        ( B ) TYPE: Nucleic Acid
        ( C ) STRANDEDNESS: Single
        ( D ) TOPOLOGY: Linear     ( i v ) ANTI-SENSE: No     ( x i ) SEQUENCE DESCRIPTION: SEQ ID NO:7:

ACAGTCTAGA CTGTTGCAGC ATCGTTCTGT G                31

( 2 ) INFORMATION FOR SEQ ID NO:8:

( i ) SEQUENCE CHARACTERISTICS:
        ( A ) LENGTH: 17 bases
        ( B ) TYPE: Nucleic Acid
        ( C ) STRANDEDNESS: Single
        ( D ) TOPOLOGY: Linear     ( i v ) ANTI-SENSE: Yes     ( x i ) SEQUENCE DESCRIPTION: SEQ ID NO:8:

GACGTTAAAG GTTGGCC                17

( 2 ) INFORMATION FOR SEQ ID NO:9:

( i ) SEQUENCE CHARACTERISTICS:
        ( A ) LENGTH: 18 bases
        ( B ) TYPE: Nucleic Acid
        ( C ) STRANDEDNESS: Single
        ( D ) TOPOLOGY: Linear     ( i v ) ANTI-SENSE: No     ( x i ) SEQUENCE DESCRIPTION: SEQ ID NO:9:

GTCTTTCATT TGGCAGTC                18

( 2 ) INFORMATION FOR SEQ ID NO:10:

( i ) SEQUENCE CHARACTERISTICS:
        ( A ) LENGTH: 129 bases
        ( B ) TYPE: Nucleic Acid ( C ) STRANDEDNESS: Single
( D ) TOPOLOGY: Linear ( i v ) ANTI-SENSE: Yes ( x i ) SEQUENCE DESCRIPTION: SEQ ID NO:10:

| | | | |
|---|---|---|---|
| CACTGGTCGC GATCGAGTTG GGACCTCCTT CGTTCTCCTC | | | 40 |
| CCTGTCTATC CTGTTTCTGT CCACTAACGA CAGTGGCCAA | | | 80 |
| TAGCTTGCTC ATCACTTTAC GTTTCTTCTT ATCTCTTTCT | | | 120 |
| TTCTCTTTC | | | 129 |

( 2 ) INFORMATION FOR SEQ ID NO:11:

( i ) SEQUENCE CHARACTERISTICS:
        ( A ) LENGTH: 292 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:11:

```
AC  ATT  GGG  AGA  AAG  TTA  GAG  AGG  TTA  GAA                           29
    Ile  Gly  Arg  Lys  Leu  Glu  Arg  Leu  Glu
                            5

GAT  TTA  AAA  AAC  AAG  ACG  CTT  GGA  GAT  TTG                           59
Asp  Leu  Lys  Asn  Lys  Thr  Leu  Gly  Asp  Leu
 10                      15

GTT  AGA  GAG  GCA  GAA  AAG  ATC  TTT  AAT  AAA                           89
Val  Arg  Glu  Ala  Glu  Lys  Ile  Phe  Asn  Lys
 20                      25

CGA  GAA  ACC  CCG  GAA  GAA  AGA  GAG  GAA  CGT                          119
Arg  Glu  Thr  Pro  Glu  Glu  Arg  Glu  Glu  Arg
 30                      35

ATC  AGG  AGA  GAA  ACA  GAG  GAA  AAA  GAA  GAA                          149
Ile  Arg  Arg  Glu  Thr  Glu  Glu  Lys  Glu  Glu
 40                      45

CGC  CGT  AGG  ACA  GAG  GAT  GAG  CAG  AAA  GAG                          179
Arg  Arg  Arg  Thr  Glu  Asp  Glu  Gln  Lys  Glu
 50                      55

AAA  GAA  AGA  GAT  AAG  AAG  AAA  CGT  AAA  GTG                          209
Lys  Glu  Arg  Asp  Lys  Lys  Lys  Arg  Lys  Val
 60                      65

ATG  AGC  AAG  CTA  TTG  GCC  ACT  GTC  GTT  AGT                          239
Met  Ser  Lys  Leu  Leu  Ala  Thr  Val  Val  Ser
 70                      75

GGA  CAG  AAA  CAG  GAT  AGA  CAG  GGA  GGA  GAA                          269
Gly  Gln  Lys  Gln  Asp  Arg  Gln  Gly  Gly  Glu
 80                      85

CGA  AGG  AGG  TCC  CAA  CTC  GAT  CG                                     292
Arg  Arg  Arg  Ser  Gln  Leu  Asp
 90                      95
```

( 2 ) INFORMATION FOR SEQ ID NO:12:

( i ) SEQUENCE CHARACTERISTICS:
        ( A ) LENGTH: 189 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:12:

| | | | |
|---|---|---|---|
| CTAGACTGTT GCAGCATCGT TCTGTGTTGT CTCTGTCTGA | | | 40 |
| CTGTGTTTCT GTATTTGTCT GASAAT ATG GGC CAG | | | 75 |

|     |     |     |     |     |     | Met | Gly | Gln |     |
|-----|-----|-----|-----|-----|-----|-----|-----|-----|-----|
| ACT | GTT | ACC | ACT | CCC | TTA | AGT | TTG | ACC | TTA |
| Thr | Val | Thr | Thr | Pro | Leu | Ser | Leu | Thr | Leu |
|     | 5   |     |     |     |     | 10  |     |     |     |

105

| GGT | CAC | TGG | AAA | GAT | GTC | GAG | CGG | ATC | GCT |
|-----|-----|-----|-----|-----|-----|-----|-----|-----|-----|
| Gly | His | Trp | Lys | Asp | Val | Glu | Arg | Ile | Ala |
|     | 15  |     |     |     |     | 20  |     |     |     |

135

| CAC | AAC | CAG | TCG | GTA | GAT | GTC | AAG | AAG | AGA |
|-----|-----|-----|-----|-----|-----|-----|-----|-----|-----|
| His | Asn | Gln | Ser | Val | Asp | Val | Lys | Lys | Arg |
|     | 25  |     |     |     |     | 30  |     |     |     |

165

| CGT | TGG | GTT | ACC | TTC | TGC | TCT | GCA |
|-----|-----|-----|-----|-----|-----|-----|-----|
| Arg | Trp | Val | Thr | Phe | Cys | Ser | Ala |
|     | 35  |     |     |     |     | 40  |     |

189